United States Patent
Boden et al.

(10) Patent No.: US 9,663,555 B2
(45) Date of Patent: May 30, 2017

(54) BETA SHEET TAPES RIBBONS IN TISSUE ENGINEERING

(71) Applicant: University of Leeds, Leeds (GB)

(72) Inventors: Neville Boden, Leeds (GB); Amalia Aggeli, Thessaloniki (GR); Eileen Ingham, Leeds (GB); Jennifer Kirkham, Leeds (GB)

(73) Assignee: University of Leeds, Leeds (GB)

( * ) Notice: Subject to any disclaimer, the term of this patent is extended or adjusted under 35 U.S.C. 154(b) by 0 days.

(21) Appl. No.: 15/234,036

(22) Filed: Aug. 11, 2016

(65) Prior Publication Data

US 2016/0340392 A1 Nov. 24, 2016

Related U.S. Application Data

(60) Division of application No. 15/066,818, filed on Mar. 10, 2016, which is a division of application No. 14/791,622, filed on Jul. 6, 2015, now Pat. No. 9,315,550, which is a division of application No. 13/551,878, filed on Jul. 18, 2012, now Pat. No. 9,101,687, which is a continuation-in-part of application No. 12/729,046, filed on Mar. 22, 2010, now Pat. No. 8,586,539, which is a continuation-in-part of application No. 10/521,628, filed as application No. PCT/GB03/03016 on Jul. 15, 2003, now Pat. No. 7,700,721.

(30) Foreign Application Priority Data

Jul. 15, 2002 (GB) .................................. 0216286.5

(51) Int. Cl.

| A61K 47/48 | (2006.01) |
|---|---|
| A61K 6/00 | (2006.01) |
| A61K 6/08 | (2006.01) |
| A61K 8/04 | (2006.01) |
| A61K 8/64 | (2006.01) |
| A61L 27/22 | (2006.01) |
| A61L 27/38 | (2006.01) |
| A61L 27/50 | (2006.01) |
| A61L 27/54 | (2006.01) |
| A61Q 19/00 | (2006.01) |
| A61Q 5/00 | (2006.01) |
| C07K 14/00 | (2006.01) |
| C12N 5/00 | (2006.01) |
| A61L 27/56 | (2006.01) |
| C07K 7/06 | (2006.01) |
| A61K 6/02 | (2006.01) |
| A61K 47/42 | (2017.01) |

(52) U.S. Cl.
CPC .......... *C07K 14/001* (2013.01); *A61K 6/0002* (2013.01); *A61K 6/02* (2013.01); *A61K 6/08* (2013.01); *A61K 8/042* (2013.01); *A61K 8/64* (2013.01); *A61K 47/42* (2013.01); *A61K 47/48246* (2013.01); *A61K 47/48784* (2013.01); *A61L 27/22* (2013.01); *A61L 27/227* (2013.01); *A61L 27/38* (2013.01); *A61L 27/50* (2013.01); *A61L 27/54* (2013.01); *A61L 27/56* (2013.01); *A61Q 5/00* (2013.01); *A61Q 19/00* (2013.01); *C07K 7/06* (2013.01); *C12N 5/0068* (2013.01); *A61K 2800/40* (2013.01); *A61L 2300/412* (2013.01); *A61L 2430/02* (2013.01); *C12N 2533/50* (2013.01)

(58) Field of Classification Search
CPC ................ A61K 2800/40; A61K 47/42; A61K 47/48246; A61K 47/48784; A61K 6/0002; A61K 6/02; A61K 6/08; A61K 8/042; A61K 8/64; A61L 2300/412; A61L 2430/02; A61L 27/22; A61L 27/227; A61L 27/38; A61L 27/50; A61L 27/54; A61L 27/56; A61Q 19/00; A61Q 5/00; C07K 14/001; C07K 7/06
USPC ................................ 514/18.6, 21.6; 530/327
See application file for complete search history.

(56) References Cited

U.S. PATENT DOCUMENTS

| 6,034,211 | A | 3/2000 | Kelly |
|---|---|---|---|
| 7,101,990 | B2 | 9/2006 | Contreras et al. |
| 7,678,883 | B2 | 3/2010 | Cheng et al. |
| 7,700,721 | B2 | 4/2010 | Boden et al. |
| 8,586,539 | B2 | 11/2013 | Boden et al. |
| 9,062,312 | B2 | 6/2015 | Rouviere et al. |
| 9,101,687 | B2 | 8/2015 | Boden et al. |
| 9,187,527 | B2 | 11/2015 | Boden et al. |
| 9,193,764 | B2 | 11/2015 | Boden et al. |
| 9,315,550 | B2 | 4/2016 | Boden et al. |
| 2003/0162696 | A1 | 8/2003 | Mihara |

(Continued)

FOREIGN PATENT DOCUMENTS

| EP | 1935438 A1 | 6/2008 |
|---|---|---|
| TW | WO 2004/069296 A1 | 8/2004 |
| TW | WO 2006/096614 A2 | 9/2006 |
| TW | WO 2008/078157 A2 | 7/2008 |
| TW | WO 2014/167310 A1 | 10/2014 |
| WO | WO 03/006494 A1 | 1/2003 |

OTHER PUBLICATIONS biowww.net/buffer-reagent/1x-Phosphate-Buffered-Saline.html (printed Mar. 22, 2010).

(Continued)

*Primary Examiner* — Julie Ha
(74) *Attorney, Agent, or Firm* — Klarquist Sparkman, LLP

(57) ABSTRACT

There is described a material comprising tapes, ribbons, fibrils or fibers characterized in that each of the ribbons, fibrils or fibers have an antiparallel arrangement of peptides in a β-sheet tape-like substructure wherein the material comprises a pair of self assembling complementary polypeptides.

18 Claims, 9 Drawing Sheets

(56) References Cited

U.S. PATENT DOCUMENTS

| | | | |
|---|---|---|---|
| 2005/0181985 | A1 | 8/2005 | Hemberger et al. |
| 2006/0154852 | A1 | 7/2006 | Boden et al. |
| 2007/0292514 | A1 | 12/2007 | Chan Pui et al. |
| 2010/0040879 | A1 | 2/2010 | Koopmans et al. |
| 2010/0040880 | A1 | 2/2010 | Koopmans et al. |
| 2010/0234304 | A1 | 9/2010 | Boden et al. |
| 2013/0012457 | A1 | 1/2013 | Boden et al. |
| 2014/0044649 | A1 | 2/2014 | Boden et al. |
| 2014/0186313 | A1 | 7/2014 | Boden et al. |
| 2015/0299266 | A1 | 10/2015 | Boden et al. |
| 2016/0046670 | A1 | 2/2016 | Boden et al. |
| 2016/0058871 | A1 | 3/2016 | Ingham et al. |
| 2016/0185824 | A1 | 6/2016 | Boden et al. |
| 2016/0199283 | A1* | 7/2016 | Hug .................. A61K 8/64 424/401 |

OTHER PUBLICATIONS

Aggeli et al., "Responsive Gels Formed by the Spontaneous Self-Assembly of Peptides Into Polymeric β-Sheet Tapes," *Nature* 386:259-262 (1997).

Aggeli et al., "Self-Assembling Homopolymeric Peptide Tapes in Aqueous Solution," Peptide Science—Present and Future (eds.), pp. 30-33 (1999).

Aggeli et al., "Structure and Dynamic of Self-Assembing β-Sheet Peptide Tapes by Dynamic Light Scattering," *Biomacromolecules* 2:378-388 (2001).

Aggeli et al., "pH as a Trigger of Peptide β-Sheet Self-Assembly and Reversible Switching between Nematic and Isotropic Phases," *J. Am. Chem. Soc.* 125:9619-9628 (2003).

Aggeli et al., "Self-assembling peptide polyelectrolyte β-sheet complexes form nematic hydrogels," Angewandte Chemie International Edition, vol. 42, pp. 5603-5606, 2003.

Bell et al., "Self-Assembling Peptides as Injectable Lubricants for Osteoarthritis," J. Biomedical Materials Res. Part A, pp. 235-246, Apr. 2006.

Carrick et al., "Effect of Ionic Strength on the Self-Assembly, Morphology and Gelation of pH Responsive β-Sheet Tape-Forming Peptides," *Tetrahedron* 63:7457-7467, 2007.

Credentist Ag, "Regenerating Teeth" from Credentis Innovation Brochure, credentis.com, printed on/or after 2012, Accessed Jun. 1, 2015.

Fishwick et al., "Structures of Helical β-Tapes and Twisted Ribbons: The Role of Side-Chain Interactions on Twist and Bend Behavior," *Nano Lett.* 3:1475-1479 (2003).

Fukushima, "Self-Induced Helix-Sheet Conformational Transitions of an Amphiphilic Peptide," *Polym. J.* 27:819-830 (1995).

Kyle et al., "Recombinant Self-Assembling Peptide as Biomaterials for Tissue Engineering," *Biomaterials* 31:9395-9405, 2010.

Nyrkova et al., "Fibril Stability in Solutions of Twisted β-Sheet Peptides: A New Kind of Micellization in Chiral Systems," *Eur. Phys. J.* 17:481-497 (2000).

Nyrkova et al., "Self-Assembly and Structure Transformations in Living Polymers Forming Fibrils," *Eur. Phys. J.* 17:499-513 (2000).

Protopapa et al., "Interaction of Self-Assembling β-Sheet Peptides with Phospholipid Monolayers: The Effect of Serine, Threonine, Glutamine and Asparagine Amino Acid Side Chains," *Electrochimical Acta* 55:3368-3375, 2010.

Riley et al., "Bioproduction and characterization of a pH responsive self-assembling peptide," Biotechnology & Bioengineering, vol. 103 (2), pp. 241-251, Jun. 1, 2009.

Zelezetsky and Tossi, "Alpha-Helical Antimicrobial Peptides—Using a Sequence Template to Guide Structure-Activity Relationship Studies," *Biochim Biophys. Acta* 1758:1435-1449, 2006.

EPSRC Details of Grant, EPSRC Reference No. EP/D070791/1, "Self assembly of GAG-functionalised peptides into proteoglycan-like molecules for tissue engineering," http://gow.epsrc.ac.uk/NGBOViewGrant.aspx?-GrantRef=EP/D070791/1, Jan. 15, 2007-Jul. 14, 2010.

GB1306338.3 Search Report dated Jan. 30, 2014 (5 pages).

PCT/GB2014/051090 International Search Report and Written Opinion dated Jun. 25, 2014 (11 pages).

\* cited by examiner

FIGURE 6A
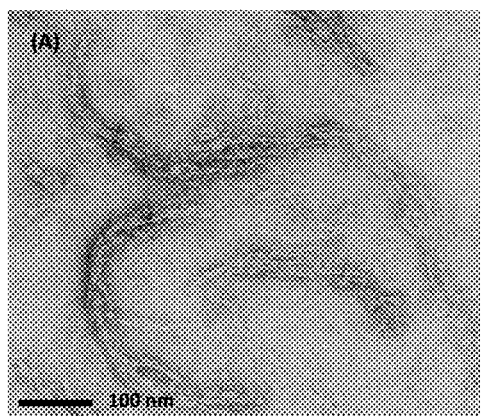
FIGURE 6B
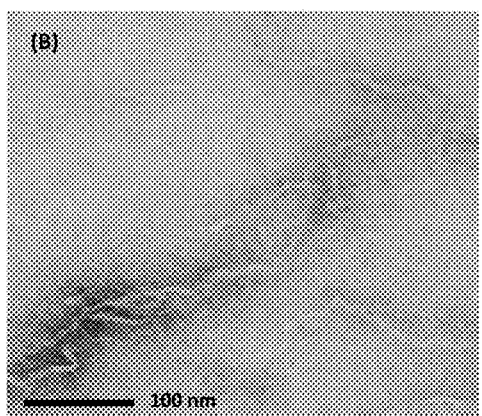
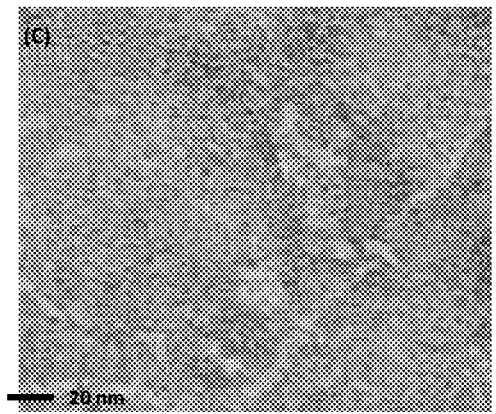
FIGURE 6C

FIGURE 7A
FIGURE 7B
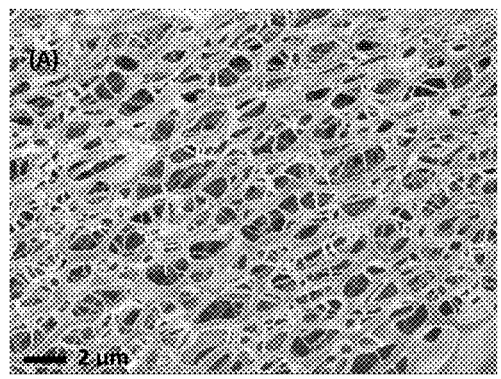
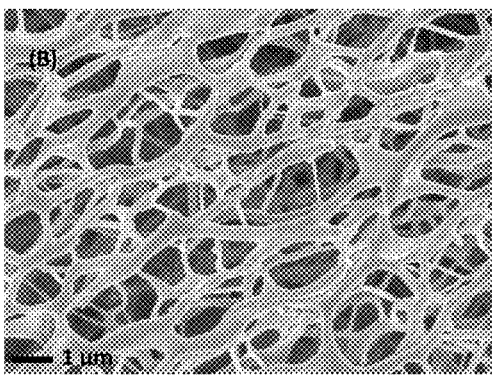
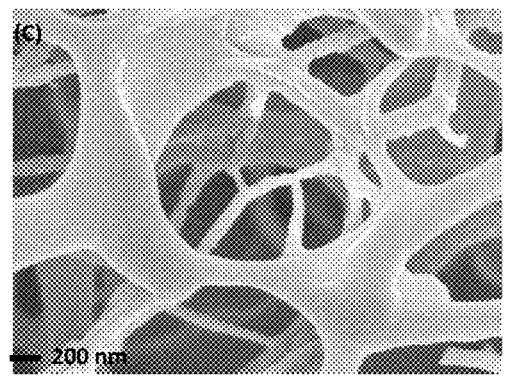
FIGURE 7C

FIGURE 8A
FIGURE 8B
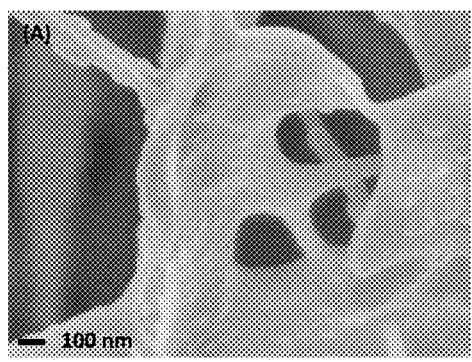 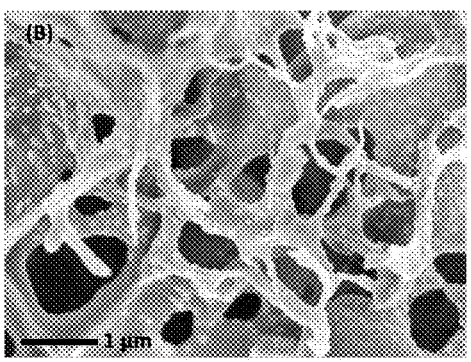
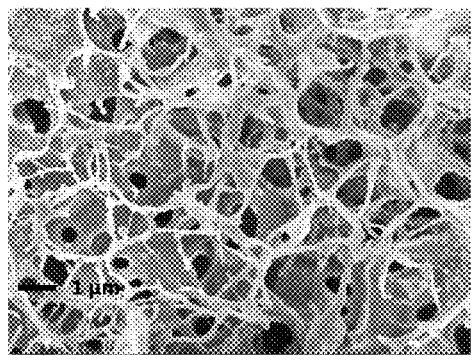 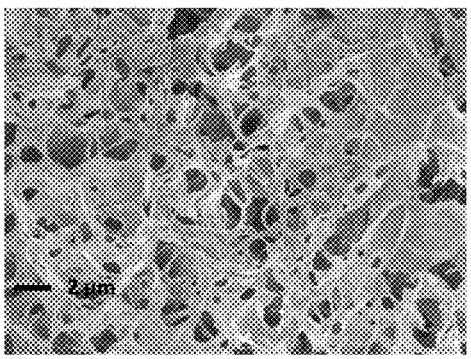
FIGURE 8C
FIGURE 8D

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: P11-4

<400> SEQUENCE: 1

Gln Gln Arg Phe Glu Trp Glu Phe Glu Gln Gln
1               5                   10

<210> SEQ ID NO 2
<211> LENGTH: 11
<212> TYPE: PRT
<213> ORGANISM: Artificial Sequence
<220> FEATURE:
<223> OTHER INFORMATION: P11-13

<400> SEQUENCE: 2

Glu Gln Glu Phe Glu Trp Glu Phe Glu Gln Glu
1               5                   10
```

```
<210> SEQ ID NO 3
<211> LENGTH: 11
<212> TYPE: PRT
<213> ORGANISM: Artificial Sequence
<220> FEATURE:
<223> OTHER INFORMATION: P11-14
<220> FEATURE:
<221> NAME/KEY: MISC_FEATURE
<222> LOCATION: (3)..(3)
<223> OTHER INFORMATION: X is an ornithine
<220> FEATURE:
<221> NAME/KEY: MISC_FEATURE
<222> LOCATION: (5)..(5)
<223> OTHER INFORMATION: X is an ornithine
<220> FEATURE:
<221> NAME/KEY: MISC_FEATURE
<222> LOCATION: (7)..(7)
<223> OTHER INFORMATION: X is an ornithine
<220> FEATURE:
<221> NAME/KEY: MISC_FEATURE
<222> LOCATION: (9)..(9)
<223> OTHER INFORMATION: X is an ornithine

<400> SEQUENCE: 3

Gln Gln Xaa Phe Xaa Trp Xaa Phe Xaa Gln Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: P11-26
<220> FEATURE:
<221> NAME/KEY: MISC_FEATURE
<222> LOCATION: (3)..(3)
<223> OTHER INFORMATION: X is an ornithine
<220> FEATURE:
<221> NAME/KEY: MISC_FEATURE
<222> LOCATION: (5)..(5)
<223> OTHER INFORMATION: X is an ornithine
<220> FEATURE:
<221> NAME/KEY: MISC_FEATURE
<222> LOCATION: (7)..(7)
<223> OTHER INFORMATION: X is an ornithine
<220> FEATURE:
<221> NAME/KEY: MISC_FEATURE
<222> LOCATION: (9)..(9)
<223> OTHER INFORMATION: X is an ornithine

<400> SEQUENCE: 4

Gln Gln Xaa Gln Xaa Gln Xaa Gln Xaa Gln Gln
1               5                   10

<210> SEQ ID NO 5
<211> LENGTH: 11
<212> TYPE: PRT
<213> ORGANISM: Artificial Sequence
<220> FEATURE:
<223> OTHER INFORMATION: P11-27

<400> SEQUENCE: 5

Glu Gln Glu Gln Glu Gln Glu Gln Glu Gln Glu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: P11-28
```

```
<220> FEATURE:
<221> NAME/KEY: MISC_FEATURE
<222> LOCATION: (1)..(1)
<223> OTHER INFORMATION: X is an ornithine
<220> FEATURE:
<221> NAME/KEY: MISC_FEATURE
<222> LOCATION: (3)..(3)
<223> OTHER INFORMATION: X is an ornithine
<220> FEATURE:
<221> NAME/KEY: MISC_FEATURE
<222> LOCATION: (5)..(5)
<223> OTHER INFORMATION: X is an ornithine
<220> FEATURE:
<221> NAME/KEY: MISC_FEATURE
<222> LOCATION: (7)..(7)
<223> OTHER INFORMATION: X is an ornithine
<220> FEATURE:
<221> NAME/KEY: MISC_FEATURE
<222> LOCATION: (9)..(9)
<223> OTHER INFORMATION: X is an ornithine
<220> FEATURE:
<221> NAME/KEY: MISC_FEATURE
<222> LOCATION: (11)..(11)
<223> OTHER INFORMATION: X is an ornithine

<400> SEQUENCE: 6

Xaa Gln Xaa Phe Xaa Trp Xaa Phe Xaa Gln Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: P11-29

<400> SEQUENCE: 7

Gln Gln Glu Phe Glu Trp Glu Phe Glu Gln Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: P11-30

<400> SEQUENCE: 8

Glu Ser Glu Phe Glu Trp Glu Phe Glu Ser Glu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: P11-31
<220> FEATURE:
<221> NAME/KEY: MISC_FEATURE
<222> LOCATION: (3)..(3)
<223> OTHER INFORMATION: X is an ornithine
<220> FEATURE:
<221> NAME/KEY: MISC_FEATURE
<222> LOCATION: (5)..(5)
<223> OTHER INFORMATION: X is an ornithine
<220> FEATURE:
<221> NAME/KEY: MISC_FEATURE
<222> LOCATION: (7)..(7)
<223> OTHER INFORMATION: X is an ornithine
<220> FEATURE:
<221> NAME/KEY: MISC_FEATURE
<222> LOCATION: (9)..(9)
<223> OTHER INFORMATION: X is an ornithine
```

```
<400> SEQUENCE: 9

Ser Ser Xaa Phe Xaa Trp Xaa Phe Xaa Ser Ser
1               5                   10
```

BETA SHEET TAPES RIBBONS IN TISSUE ENGINEERING

CROSS REFERENCE TO RELATED APPLICATIONS

This is divisional of U.S. application Ser. No. 15/066,818 filed Mar. 10, 2016, which is a divisional of U.S. application Ser. No. 14/791,622 filed Jul. 6, 2015, now U.S. Pat. No. 9,315,550, which is a divisional of U.S. application Ser. No. 13/551,878 filed Jul. 18, 2012, now U.S. Pat. No. 9,101,687, which is a continuation-in-part application of U.S. application Ser. No. 12/729,046 filed Mar. 22, 2010, now U.S. Pat. No. 8,586,539, which is a continuation-in-part application of U.S. application Ser. No. 10/521,628 filed Sep. 8, 2005, now U.S. Pat. No. 7,700,721 (all herein incorporated by reference), which is the U.S. National Stage of International Application No. PCT/GB2003/003016, filed Jul. 15, 2003 (published in English under PCT Article 21(2)), which in turn claims the benefit of Great Britain patent application no. 0216286.5 filed Jul. 15, 2002.

FIELD

This disclosure relates to novel supramolecular aggregates, polymers and networks made by beta-sheet self-assembly of rationally-designed complementary peptides, and their uses as for example as responsive industrial fluids (oil exploration), as personal care products, as tissue reconstruction devices (e.g., dental reconstructive devices), or as controlled drug delivery systems.

BACKGROUND

International Patent Application No WO 96/31528 (Boden et al.) describes novel rationally designed peptides which self-assemble in one dimension to form beta sheet tape-like polymers. The tapes above a critical peptide concentration (typically above 0.3% v/v peptide) become physically entangled and gel their solutions in organic solvents or in water. The monomeric or single peptide gels possess the specific property of being programmable to switch from the gel state to a fluid or stiffer gel state in response to external chemical or physical triggers. The self-assembly of peptides into beta tape aggregates follows a hierarchical system, as the concentration of peptide increases they will begin to form beta tapes, as the concentration of peptide increases further two beta tapes will interact with each other to form a ribbon, as the concentration of peptide increases yet further ribbons will interact with each other to form fibrils and finally if the concentration increases high enough fibrils can interact to form fibres.

It has recently been found that the tapes having chemically distinct opposing surfaces can give rise to an hierarchy of other self-assembled, supramolecular structures as a function of increasing peptide concentration: ribbons (two stacked tapes), fibrils (many ribbons stacked together) and fibres (entwined fibrils). All these beta-sheet polymers appear twisted because of the peptide chirality. A theoretical model has been developed which rationalises this self-assembly process of beta-sheet forming peptides using a set of energetic parameters $\epsilon_j$. The magnitudes of $\epsilon_j$ define the peptide concentration ranges over which each type of polymer will be stable.

Complementary peptide gels are a special case of peptide gels. The main differences between single peptide gels and complementary peptide gels are that in single peptide gels, gelation can be triggered by specific environmental conditions typically specific pH and/or salinity. This property can create a problem in the case of usage of peptide gels in medical applications, i.e. the peptide fluid solution eg in pure water, hits the physiological solution and immediately transforms into a gel, which can act like a gel plug, preventing further diffusion of the peptide solution to fill a large cavity or to form an interpenetrated network inside another porous matrix for example a decellularised tissue matrix. In the case of the complementary peptide gels, it is possible to overcome this problem by administering first peptide A which is in a low viscosity fluid monomeric state, this is then followed by administering the complementary peptide B which is also in a low viscosity fluid monomeric state. In this case, the formation of the peptide gel network only takes place by the coexistence of A and B in the same volume and their interaction and self-assembly (FIG. 1), rather by the presence of any other chemical or physical conditions of the solution, i.e. pH, salinity or specific counterions e.g., Ca+2. This makes complementary peptide gelation in situ a much more reliable event and much more likely to happen in the whole space that is available rather than only at the entrance point of a cavity or only on the surface of a porous material.

A further difference between single peptide and complementary peptide self-assembly is that the latter typically relies on complementary intermolecular electrostatic interactions. This causes very high affinity between adjacent self-assembling peptides, much higher than it would normally by achieved by single peptide self-assembly. Since the affinity between complementary peptides is expected to be higher than for single peptides, then the critical concentration (c*tape) for tape self-assembly will be expected to be much lower for complementary peptides than for single peptide tapes. The magnitude of c*tape (FIG. 2) relates to how fast or how slow a peptide gel will dissolve out of the injection site in situ. Peptide gels that are required to have as long a lifetime as possible in vivo, must have as low c*tape value as possible. Therefore complementary peptides provide a way to form an injectable gel in situ that will be expected to be much more long lived and therefore acting for much longer in vivo, than their corresponding single peptide gels.

A yet further difference between single peptide tapes and complementary peptide tapes is that the complementary ones provide a lot more surface versatility than single peptide gels because they consist of alternating peptides A

SUMMARY

We have shown that by appropriate peptide design we can produce polymers comprising tapes, ribbons, fibrils or fibres by simply mixing a pair of complementary peptides irrespective of controllable environmental conditions or changes such as the pH, the ionic strength of the solution or temperature. In particular, complementary peptides can be designed which, when combined, self-assemble to form one or other of these polymers.

We have recently discovered that this hierarchy of polymers can be formed by mixing complementary peptides together (alternating co-polymers). For example, we have shown that complementary peptide $P_{11}$-13 and $P_{11}$-14 (Table 1A and 1B) when contacted together immediately undergo gelation, in all cases of the complementary peptides of the present invention apart from $P_{11}$-26/27, gelation took place instantly upon mixing of the separate fluid monomeric peptide solutions at all concentration equal to or higher than c*gel. The formed gel remained stable over time confirming apparent equilibrium behaviour, the complementary peptides of the present invention provide significant advantages over the prior art monomeric peptides having an overall net charge of +/−2 as there is no requirement for controlling environmental conditions such as pH, salinity or presence of specific counterions such as $Ca^{++}$.

According to the present invention there is provided alternate co-polymer beta-sheet polymeric tapes, ribbons, fibrils and fibres made by the self-assembly of more than one complementary peptides. The complementarity of the peptide originating from their charges e.g., net positive charge on one peptide and net negative charge on the other peptide to provide an overall net charge of +/−2 per pair of complementary peptides and under standard physiological conditions of pH and salt.

Reference herein to complementary peptides indicates that the overall net charge of a combination of separate solutions of peptides is either +/−2, it has been found that the overall net charge of, for example the negative −2 ($P_{11}$-13/14) or positive +2 ($P_{11}$-28/29), makes little difference in the gelation, morphology and self-assembly behaviours of the complementary peptides. However, completely polar complementary peptides don't form gels in physiological solutions, rather they tend to phase separate from solution, possibly either due to many defects forming during the self assembly process or due to very strong hydrogen bond interactions between then multiple —$CONH_2$ groups on the surfaces of these tapes.

Thus, provided herein is a material comprising ribbons, fibrils or fibres characterised in that each of the ribbons, fibrils or fibres have an antiparallel arrangement of peptides in a β-sheet tape-like substructure.

When the material substantially comprises fibrils, the fibrils may be comprised in a network of fibrils interconnected at fibre-like junctions.

Also provided is a material wherein the material comprises self assembling complementary peptides (SACPs) wherein the SACPs form a tape in an aqueous medium and is made up of 3 or more polar/neutral amino acids and a plurality of charged amino acids but wherein the overall net charge is +/−2 per pair of complementary peptides.

The polar/neutral amino acids, which may be the same or different, can be selected from the group including glutamine, serine, asparagine, ornithine, threonine, tyrosine, glutamic acid, phenylalanine and tryptophan.

We further provide a material wherein the complementary peptides are overall +2 positively charged per pair of peptides and form a gel when the first of the complementary monomeric peptides contacts its complementary second monomeric peptide ($P_{11}$-28/29). Alternatively, we provide a material wherein the complementary peptides are overall −2 negatively charged per pair of peptides ($P_{11}$-13/14; $P_{11}$-30/31; $P_{11}$-26/27) and form a gel when the first and second complementary peptides of the pair make contact with one another.

We further provide a material wherein the amino acid chain is extended to include a bioactive peptide sequence, or wherein the amino acid chain is attached to a therapeutically active molecule.

The material may comprise SACPs which forms ribbons and/or fibrils in an aqueous solution and wherein the SACPS has a primary structure in which at least 50% of the amino acids comprise an alternating structure of polar and apolar amino acids.

The polar amino acids include from 4 to 6 charged amino acids per 11 amino acids. Preferably, the SACPs are selected from the group comprising: $P_{11}$-13/14 (SEQ ID NOs: 2 and 3); $P_{11}$-26/27 (SEQ ID NOs: 4 and 5); $P_{11}$-28/29 (SEQ ID NOs: 6 and 7) and $P_{11}$-30/31 (SEQ ID NOs: 8 and 9).

Exemplary complementary peptides of the present disclosure are recited in Tables 1A- and 1B.

TABLE 1A

Primary structures of rationally designed complementary peptides.

| Peptide Name | Primary Structure* | SEQ ID NO: |
|---|---|---|
| $P_{11}$-4 | $CH_3CO$—Q—Q—R—F—E—W—E—F—E—Q—Q—$NH_2$ | 1 |
| $P_{11}$-13 | $CH_3CO$—E—Q—E—F—E—W—E—F—E—Q—E—$NH_2$ | 2 |
| $P_{11}$-14 | $CH_3CO$—Q—Q—O—F—O—W—O—F—O—Q—Q—$NH_2$ | 3 |
| $P_{11}$-26 | $CH_3CO$—Q—Q—O—Q—O—Q—O—Q—O—Q—Q—$NH_2$ | 4 |
| $P_{11}$-27 | $CH_3CO$—E—Q—E—Q—E—Q—E—Q—E—Q—E—$HN_2$ | 5 |
| $P_{11}$-28 | $CH_3CO$—O—Q—O—F—O—W—O—F—O—Q—O—$NH_2$ | 6 |
| $P_{11}$-29 | $CH_3CO$—Q—Q—E—F—E—W—E—F—E—Q—Q—$NH_2$ | 7 |
| $P_{11}$-30 | $CH_3CO$—E—S—E—F—E—W—E—F—E—S—E—$NH_2$ | 8 |
| $P_{11}$-31 | $CH_3CO$—S—S—O—F—O—W—O—F—O—S—S—$NH_2$ | 9 |

*The N— and C— termini of the peptides are always blocked with $CH_3CO$— and $NH_2$— respectively.
O symbolizes ornithine amino acid side chains.

TABLE 1B

Self assembling complementary peptides.

| Peptide | One letter amino acid code | Charge | Affect being studied | Structure |
|---|---|---|---|---|
| $P_{11}$-13 | AcEQEFEWEFEQENH$_2$ | −6 | N/A | 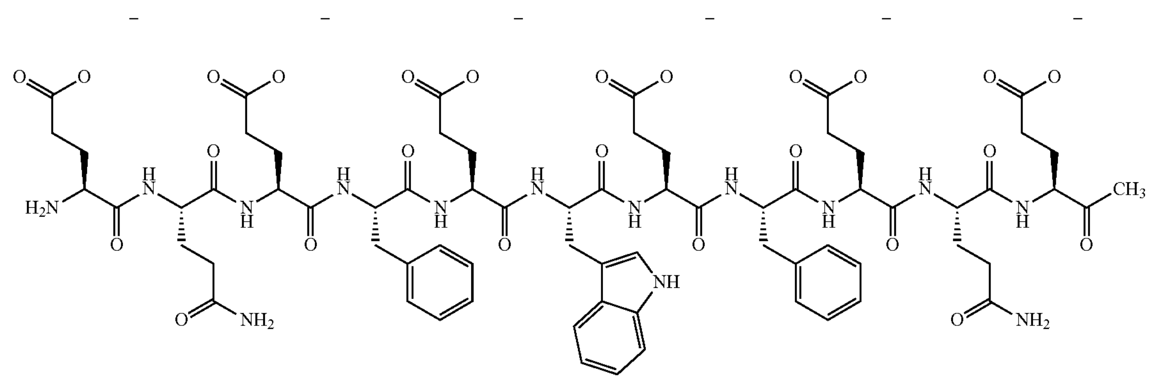 [SMILES: CC(=O)[C@H](CCC(=O)O)NC(=O)[C@H](CCC(N)=O)NC(=O)[C@H](CCC(=O)O)NC(=O)[C@H](Cc1ccccc1)NC(=O)[C@H](CCC(=O)O)NC(=O)[C@H](Cc1c[nH]c2ccccc12)NC(=O)[C@H](CCC(=O)O)NC(=O)[C@H](Cc1ccccc1)NC(=O)[C@H](CCC(=O)O)NC(=O)[C@H](CCC(N)=O)NC(=O)[C@@H](N)CCC(=O)O] |
| $P_{11}$-14 | AcQQOQOFOWOFOQQNH$_2$ | +4 | N/A | 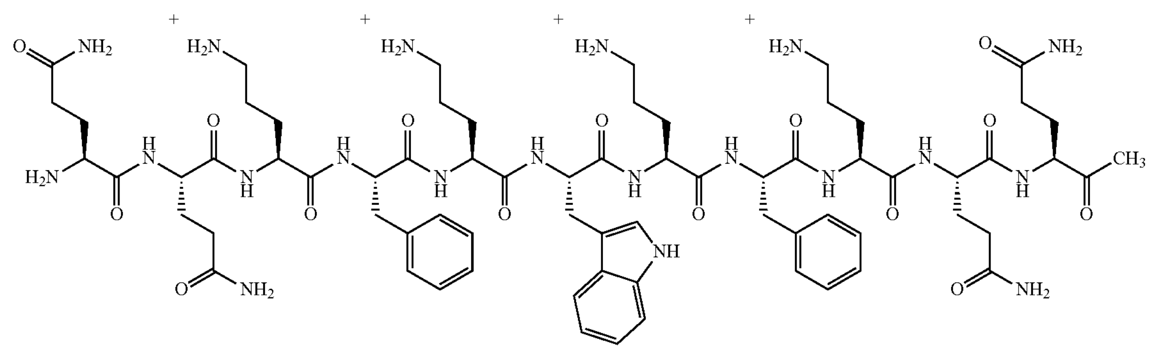 [SMILES: CC(=O)[C@H](CCC(N)=O)NC(=O)[C@H](CCC(N)=O)NC(=O)[C@H](CCCN)NC(=O)[C@H](Cc1ccccc1)NC(=O)[C@H](CCCN)NC(=O)[C@H](Cc1c[nH]c2ccccc12)NC(=O)[C@H](CCCN)NC(=O)[C@H](Cc1ccccc1)NC(=O)[C@H](CCCN)NC(=O)[C@H](CCC(N)=O)NC(=O)[C@@H](N)CCC(N)=O] |

TABLE 1B-continued

Self assembling complementary peptides.

| Peptide | One letter amino acid code | Charge | Affect being studied | Structure |
|---|---|---|---|---|
| P₁₁-26 | AcQQQQOQQQQQQNH₂ | +4 | Polarity | |
| P₁₁-27 | AcEQEQEQEQEQENH₂ | -6 | Polarity | |

TABLE 1B-continued
Self assembling complementary peptides.
| Peptide | One letter amino acid code | Affect being studied | Structure |
|---|---|---|---|
| P₁₁-28 | AcOQOFOWOFOQQNH₂ | +6 Charge | 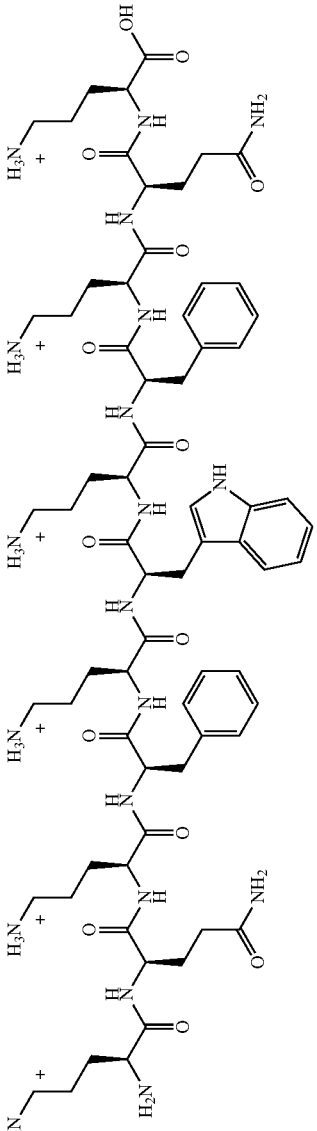 |
| P₁₁-29 | AcQQEFEWEFEQQNH₂ | −4 Charge | 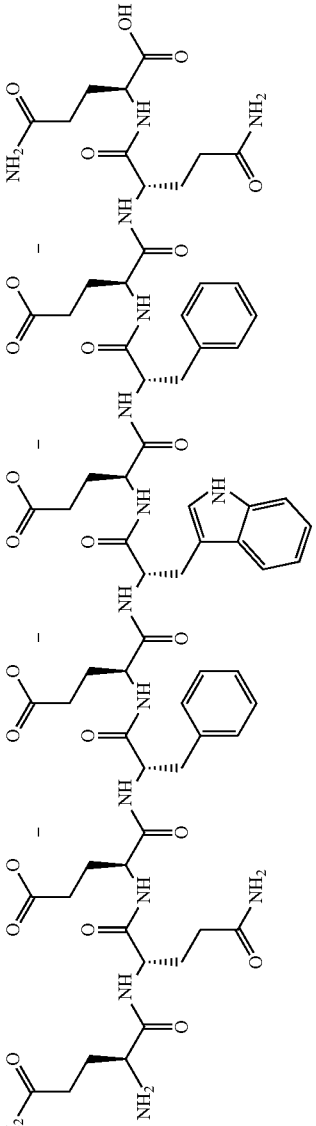 |

TABLE 1B-continued

Self assembling complementary peptides.

| Peptide | One letter amino acid code | Charge | Affect being studied | Structure |
|---|---|---|---|---|
| P₁₁-30 | AcESEFEWEFESENH₂ | −6 | Serine | |
| P₁₁-31 | AcSSOFOWOFOSSNH₂ | +4 | Serine | |

The peptides provided herein are preferably 11 residues in length.

Preferably, in each complementary pair the amino acids at positions 2, 4, 6, 8, and 10 are the same. For example, the complementary pair $P_{11}$-13/14 each have glutamine, phenylalanine, tryptophan phenylalanine and glutamine at positions 2, 4, 6, 8, 10 respectively as has the complementary pair $P_{11}$-28/29. The complementary peptides of $P_{11}$-26/27 have glutamine at all five positions and $P_{11}$-30/31 has serine, phenylalanine, tryptophan, phenylalanine and serine at positions 2, 4, 6, 8, 10 respectively.

Preferably the amino acid at position 2 is either glutamine or serine, at position 4 it is either phenylalanine or glutamine, at position 6 it is either tryptophan or glutamine, at position 8 it is either phenylalanine or glutamine and at position 10 it is either serine or glutamine.

Preferably, the amino acid residues at positions 10 and 11 of one of the complementary monomeric peptides are the same and are selected from the group comprising serine (SS) or glutamine (QQ) Peptides $P_{11}$-14/26/29 each have glutamine at positions 10 and 11 whereas $P_{11}$-31 has serine at the terminal two positions.

Preferably, the amino acid residue at position 4 is either phenylalanine or glutamine.

Preferably, the amino acid residues at positions 4 and 5 are selected from the pairs of the group comprising phenylalanine and glutamic acid, phenylalanine and ornithine, glutamine and glutamic acid and glutamine and ornithine.

Preferably, the terminal hydrogen bond group is either —CONH$_2$ or OH. The presence of —CONH$_2$ hydrogen bonding moieties ($P_{11}$-13/14 and $P_{11}$-28/29) on the surface of the tapes appear to be more efficient than —OH hydrogen bond moieties ($P_{11}$-30/31) in creating gels with lower c*gel with much more well defined tape self-assembly and lower c*tape therefore providing a potentially longer lifetime in vivo.

The material may be suitable for use in, inter alia, tissue engineering, cell culture medium, and/or dental treatment. The complementary peptides of the present invention are considered as ideal candidates for regenerative medicine as self assembly does not occur until both monomers are mixed together which makes application within the body more achievable and overcomes the problem of gel plug formation.

We also provide a material wherein the material comprises self assembling complementary peptides (SACPs) wherein the SACPS forms a tape in an aqueous medium and wherein each complementary peptide is made up of 3 or more polar/neutral amino acids and a plurality of charged amino acids.

In some examples, the SACPS are isolated. An "isolated" biological component (such as a protein) has been substantially separated or purified away from other biological components present in the cell of an organism, or the organism itself, in which the component may naturally occur, such as other chromosomal and extra-chromosomal DNA and RNA, proteins and cells. In addition, proteins that have been "isolated" include proteins purified by standard purification methods. The term also embraces proteins prepared by recombinant expression in a host cell as well as chemically synthesized proteins. For example, an isolated SACP is one that is substantially separated from other peptides.

The polar/neutral amino acids, which may be the same or different, may be selected from the group including glutamine, serine, asparagine, ornithine, threonine, tyrosine, glutamic acid, tryptophan and phenylalanine.

In one example, the SACPs have a polar amino acid selected from the group consisting of serine, threonine, tyrosine, asparagine, and glutamine.

The apolar amino acids, which may be the same or different, are selected from the group including phenylalanine, leucine, isoleucine, valine and tryptophan.

We further provide a material wherein the amino acid chain is extended to include a bioactive peptide sequence, or wherein the amino acid chain is attached to a therapeutically active molecule.

We also provide a material wherein the SACPs are soluble and may comprise a ratio of net charged amino acids to total amino acids of from 6:11 to 4:11.

The material may be suitable for use in, inter alia, tissue engineering, cell culture medium, and/or dental treatment.

We further provide a material wherein the complementary peptide tapes are made up of 3 or more polar amino acids of which some are charged amino acids wherein the ratio of charged amino acids to total amino acids is 4:11 or greater.

Also provided is a composition that includes ribbons, fibrils or fibres and wherein the complementary peptides are present at a concentration of at least 1 mg/ml in the composition (for example 1 mg/ml to 100 mg/ml, 1 mg/ml to 60 mg/ml, 1 mg/ml to 50 mg/ml, 1 mg/ml to 35 mg/ml, 15 mg/ml to 15 mg/ml or 20 mg/ml to 35 mg/ml and any other integers therebetween). Each of the ribbons, fibrils or fibres has an antiparallel arrangement of peptides in a β-sheet tape-like substructure, wherein each pair of complementary peptides comprises a net −2 or a +2 charge, and wherein the peptide is selected from the group comprising $P_{11}$-13/14 (SEQ ID NOs: 2 and 3); $P_{11}$-26/27 (SEQ ID NOs: 4 and 5); $P_{11}$-28/29 (SEQ ID NOs: 6 and 7) and $P_{11}$-30/31 (SEQ ID NOs: 8 and 9). as set forth in Table 1A.

The foregoing and other features of the disclosure will become more apparent from the following description of the figures.

BRIEF DESCRIPTION OF THE FIGURES

FIG. 5A shows 15 mg/ml times dilution magnification of FIG. 5B 15 mg/ml at 15 times dilution magnification of 52,000 times.

FIGS. 6A-6C show TEM images of the complementary peptides $P_{11}$-30/31. FIG. 6A shows 20 mg/ml diluted 15 times, magnification 52,000 times, FIG. 6B 20 mg/ml diluted 15 times magnification of 52,000 times and FIG. 6C 20 mg/ml diluted 15 times, magnification of 39,000 times.

FIGS. 7A-7C show SEM images of the complementary peptides $P_{11}$-13/14 30 mg/ml at magnification of (A) 5,000, (B) 10,000 and (C) 35,000 times.

FIGS. 8A-D show SEM images of the complementary peptides $P_{11}$-30/31 15 mg/ml at magnification of (A) 70,000, (B) 20,000, (C) 10,000 times and (D) 5,000 times.

SEQUENCE LISTING

Figure 1:
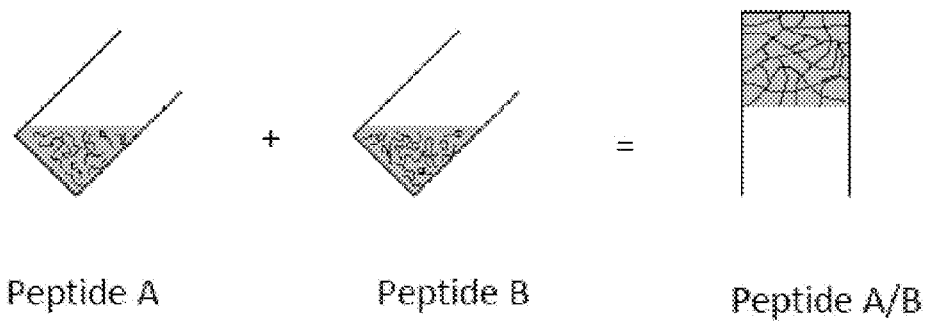
FIG. 1 illustrates the mixing of monomeric complementary peptides that are originally in separate, low viscosity solutions, triggers peptide self-assembly and instant gelation.
Figure 2:
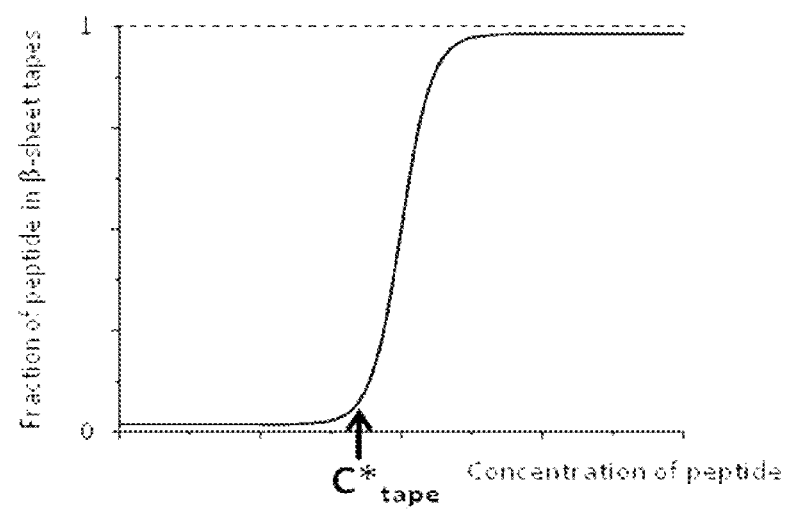
FIG. 2 shows a typical self-assembly curve, indicating the onset point for self-assembly.
Figure 3:
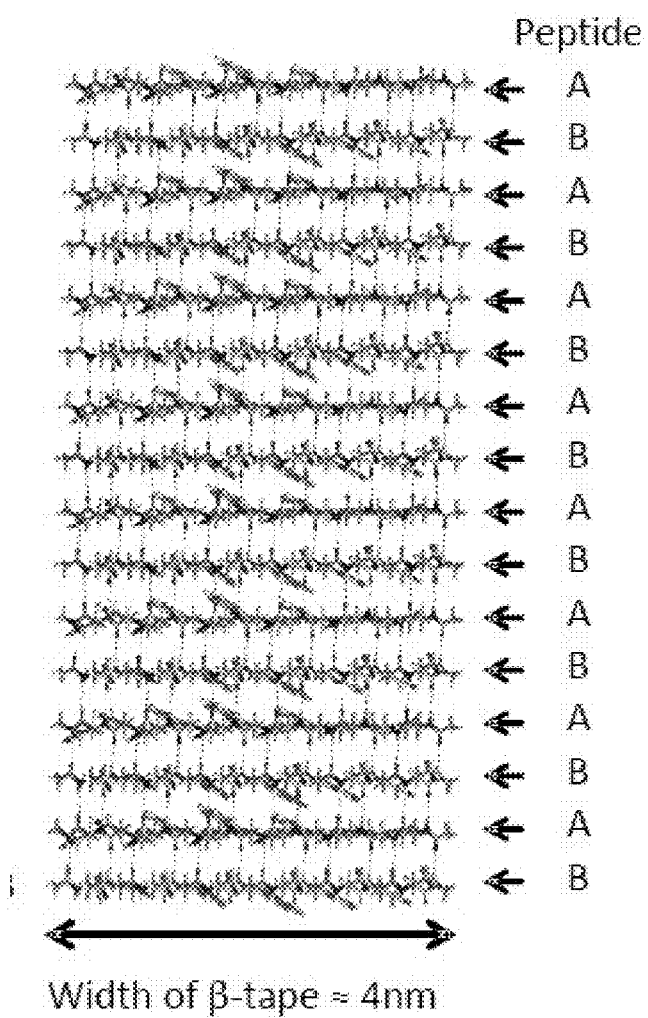
FIG. 3 represents a complementary peptide tape.

The protein sequences listed in the accompanying sequence listing are shown using standard letter abbreviations for proteins. The Sequence Listing is submitted as an ASCII text file, created on Jul. 12, 2016 8 KB, which is incorporated by reference herein.

SEQ ID NO: 1 is the amino acid sequence for P11-4.
SEQ ID NO: 2 is the amino acid sequence for P11-13.
SEQ ID NO: 3 is the amino acid sequence for P11-14.
SEQ ID NO: 4 is the amino acid sequence for P11-26.
SEQ ID NO: 5 is the amino acid sequence for P11-27.
SEQ ID NO: 6 is the amino acid sequence for P11-28.
SEQ ID NO: 7 is the amino acid sequence for P11-29.
SEQ ID NO: 8 is the amino acid sequence for P11-30.
SEQ ID NO: 9 is the amino acid sequence for P11-31.

DETAILED DESCRIPTION

The singular forms "a," "an," and "the" refer to one or more than one, unless the context clearly dictates otherwise. For example, the term "comprising a peptide" includes single or plural peptide and is considered equivalent to the phrase "comprising at least one peptide." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

We have also shown that above a certain peptide concentration $c_{I/N}$ (isotropic to nematic transition concentration) the semi-rigid ribbons, fibrils and fibres can align and thus transform their initially isotropic solution into a nematic liquid crystalline solution. The transition of the solution to the nematic liquid crystalline state happens at lower concentrations for more rigid polymers.

We have also shown that as the peptide concentration increases even further there is a second transition from a fluid nematic liquid crystalline solution to a self-supporting nematic gel, which is formed by the entwining of the fibrils.

We have discovered that the alignment of these polymers (tapes, ribbons, fibrils and fibres) can be improved significantly by shearing or application of external magnetic field to the peptide solution. Subsequent gelation locks the aligned polymers into place and preserves their alignment for a long time (typically weeks) even after the polymer solution is removed from the magnetic field or after the end of shearing. Shearing or external magnetic field (superconducting magnet with a field strength of 7T) have been found indeed to improve the alignment of fibrils in aqueous solutions, as shown by monitoring the birefringence of the solution using cross polars. The improved polymer alignment in solution has been preserved for several weeks after the end of shearing or of the application of the magnetic field.

Provided is a method of producing nematic liquid crystalline solutions and gels of alternating copeptide beta-sheet tapes, ribbons, fibrils or fibres with improved polymer alignment and thus improved optical properties (i.e., increased liquid crystallinity and birefringence), by shearing the peptide solutions or by subjecting them to other external forces such as electric and magnetic fields.

These peptide liquid crystalline solutions and gels can be formed in organic solvents or in water depending on the peptide design. The design of the complementary peptide primary structure is necessary to achieve compatibility between the surface properties of the peptide polymers and the solvent. For example, self-assembling beta-sheet forming peptides with predominantly hydrophobic amino acid side-chains are required to form nematic solutions and gels in moderately polar solvents, whilst peptides which form tapes with at least one polar side are required to obtain nematic solutions and gels in water.

The fibrils and fibres are alignable and can therefore form nematic gels. Therefore, the fibrils and fibres can be spun to make, for example, high tensile strength fibres, cf. Kevlar®. Also, they can be used to make highly ordered scaffolds for tissue engineering or templates for the growth of inorganic matrices, or as matrices for the alignment of biomolecules, e.g., in NMR spectroscopy.

Until recently, formation of these polymers has been limited to relatively simple solutions (e.g., pure solvents or low ionic strength solutions). We have now discovered that it is possible to rationally design pairs of complementary peptides which will form soluble polymers (e.g., tape, ribbons, fibrils and fibres) once they have been mixed together or allowed to contact one another.

The stages of complementary peptide design for formation of soluble beta-sheet polymers and gel scaffolds are:
1) for production of single tapes, design the peptide following the criteria in the International Patent Application No. PCT/GB96/00743. To produce stable single tapes in cell media, both sides of tapes should be covered by predominantly polar groups.
2) for production of ribbons, fibrils and fibres, one sides of the tape should be different from the other, e.g. one predominantly polar and the other predominantly apolar. The polar sides should also be able to weakly interact with each other e.g. through hydrogen-bonding sites provided for example by glutamine or asparagines side chains.
3) To ensure all these polymers are soluble, some repulsion between polymers must be created. This can be electrostatic repulsion between like charges on the polymers. Alternatively, it can be steric repulsions created by flexible solvophilic chains decorating the peptide polymers such as polyethylene glycol chains when water is the preferred solvent. These PEG segments can be attached on amino acid side-chains or on the peptide termini.

By way of illustration, we include the following example:
A large number (dozens) of systematically varied peptides (typically 7-30 residues long) have been studied for soluble polymer and gel formation. All of these peptides can self-assemble to form beta-sheet polymers in certain low-ionic strength media, but most were found to precipitate out of solution in cell media. Only complementary peptides with a approximate net +2 or −2 charge per peptide pair, were able to form soluble polymers in gel cell media (The amount of net charge necessary per peptide to keep its complementary polymers soluble will vary depending on the overall surface properties and solubility of the peptide tapes it forms).

The fibrils entwine and form a three dimensional network and turn their solution into a homogeneous self-supporting gel at peptide concentration higher than 1 to 5 mg/ml. The gel remains stable for at least several weeks at room temperature.

The gel can be broken by mechanical agitation. The time it takes to reform depends on the complementary peptide concentration, ranging from seconds for a 15 mg/ml peptide gel, to hours for a 1 mg/ml peptide gel.

Thus, peptide fibrils and gels with a variety of chemical properties can be produced by complementary peptide design. For example, the type of charge (+ or −) of the polymer may be crucial for the polymer matrix-cell interactions. The nature of the neutral polar side-chains can also be varied to fine-tune and maximise the favourable polymer-cell interactions, and the polymer stability in vivo.

The fibrils and gels can reform after sterilisation using an autoclave. Thus autoclaving is a viable method to sterilise these peptide gels. This is significant, since sterilisation is a prerequisite for the use of these materials with cells in vitro or in vivo. Other alternative sterilisation methods that can also be used are filtration of the initially monomeric peptide solutions or gamma irradiation.

Although the peptide design procedure stated above can be used to design either tapes or higher order aggregates (i.e., ribbons, fibrils and fibres) the more robust fibrils and fibres are potentially more useful for production of complementary peptide scaffolds for tissue engineering. The reason is that the fibrils being much stronger structural units than e.g., tapes, can support cells in three dimensions without significant breakage for a long time. In addition, the highly packed nature of the fibrils, protects the peptides from enzymatic degradation, and can increase significantly the lifetime of the scaffold in vivo.

The peptide gels are formed with a very low complementary peptide concentration (typically at or above 5 mg/ml), which corresponds to 0.003 volume fraction of peptide and 0.997 volume fraction of solvent in the gel, which means that the gels contain mainly solvent. Thus, encapsulated cells in these gels, have a lot of room available to grow, to communicate with each other and nutrients, oxygen, and various metabolites can diffuse almost freely in and out of the gel network.

The opportunities that these new biomaterials provide for tissue engineering in vitro and in vivo are enormous. A large number of different cells can be encapsulated in these polymer scaffolds.

Complementary peptides can be designed to have a self-assembling domain followed by at least one bioactive domain. Thus, polymeric gel scaffolds can be formed in cell media, decorated with specific bioactive sequences (e.g., RGD sequence) which will control the interactions of the scaffold with a particular type of cell, and also influence the growth differentiation state and function of the encapsulated cells.

The complementary peptide polymers (especially so the more rigid fibrils and fibres) can be preferentially aligned by shearing or application of magnetic field. Thus, anisotropic polymer scaffolds can be obtained which when they are seeded with cells, they can be particularly important for the control of cell type, cell-cell interactions and shape of the growing tissue.

The cells can be encapsulated in the polymer matrix in a variety of different ways. For example:

1) disruption of gel by mechanical agitation, mixing with the cells, and encapsulation of the cells as the gel matrix reforms around them.
2) Mix the cells with an initially fluid first monomeric peptide solution in cell media, followed by triggered gel formation on contact with its complementary peptide.

Possibly the most effective way of encapsulating cells in the peptide scaffolds is using alternating copeptides.

It is seen that the alternating copeptide systems offer a unique way of encapsulating cells in the peptide scaffolds without the need to change the pH, ionic strength and counter ion concentration of the cell solutions. This can be done by mixing the cells with one of the initial monomeric peptide solutions, and subsequently adding the complementary peptide solution.

The heteropeptide polymers scaffolds also offer the advantage of combining different functionalities on the same polymers, and extending the chemical and periodic features of homopeptide polymers. For example one peptide component of the polymer may have a bioactive peptide bound to it, whilst its other complementary peptide compound may have a drug molecule bound on it.

The ribbons, fibrils and/or fibres of the disclosure exhibit significant tensile strength, controlled, inter alia, by how many tapes make up the ribbons, fibrils or fibres, especially in the longitudinal direction of the fibril or fibre. Such strength has been estimated to be in the order of that of a conventional covalent bond. Furthermore, since the fibrils and/or fibres are biodegradable, because of their peptide content, they are especially advantageous in that they may be constructed into a biodegradable scaffold. Such scaffolds may comprise a weave, knit or plait of the fibrils or fibres of the disclosure.

Scaffolds can also be constructed using a combination of the complementary peptide polymers and other commercial polymers (such as cotton and wool fibres), to obtain materials with a desirable combination of mechanical, chemical and biochemical properties, and low production cost.

Alignment of the microscopic fibrils followed by subsequent lateral association of the fibrils can result in the formation of macroscopic oriented fibre mats.

The peptide fibrils and/or fibres can be engineered to control the chemical and bioactive properties of synthetic polymer fibres. The methodology has the advantage of harnessing and combining existing expertise on manufacturing at low-cost well controlled fibrous structures with desirable mechanical properties, with the opportunity of designing their bioactivity, biocompatibility and other chemical properties. Such new materials can have exciting applications in biomedical fields such as in tissue engineering, wound healing and tissue adhesion.

Products and Applications
Industrial Applications

Modification of the physical and chemical properties of a surface in a controlled way, e.g., wetting properties; for example, for anti-icing applications.

Also for controlling the interaction of oil/water with clay surfaces, and the stabilising the clay itself, an important issue when, e.g., dealing with fractures in oil wells. The stability of the peptide polymers can be controlled by peptide design. Thus, by increasing the number of amino acid residues per peptide and also the number of favourable intermolecular interactions between amino acid side-chains, complementary peptide polymers with increased stability and strength can be obtained. In addition, ribbons, fibrils and fibres can be increasingly more stable polymers compared to single tapes. Thus, the right polymers can be produced by complementary peptide design to form gels stable in the high temperature of the oil wells. These gels can for example provide significant mechanical support at a specific site of the oil well.

Receptor or receptor binding sites can be engineered by complementary peptide design into the ribbons, fibrils and/or fibres, providing materials for use as sensors or as biocatalysts, or as separation media in biotechnology applications.

The peptide tapes, ribbons, fibrils and fibres can be used as templates for the production of nanostructured inorganic materials with chiral pores. The dimensions, pitch and chirality of the pores can be controlled by peptide design to control the properties of the polymer aggregate. The orientation of the pores can also be controlled by alignment of the polymers in nematic states. These nanostructured materials have important applications as chiral separation media.

The fibres of the disclosure are advantageous because, inter alia, they possess similar properties to other known peptide fibres, for example, KEVLAR® which consists of long molecular chains produced from poly-paraphenylene terephthalamide. Thus the fibres of the disclosure exhibit the following features: high tensile strength at low weight, high modulus, high chemical resistance, high toughness, high cut resistance, low elongation to break, low thermal shrinkage, high dimensional stability, flame resistant and self extinguishing.

Therefore, the fibres of the disclosure can be processed into various forms, for example, continuous filament yarns, staple, floc, cord and fabric.

The processed fibres may possess the following characteristics: continuous filament yarn, high tensile strength, processable on conventional looms, twisters, cord forming, stranding and serving equipment; staple, very high cut resistance, spun on conventional cotton or worsted spinning equipment, precision cut short fibres, processable on felting and spun lace equipment; pulp-wet and dry, floc, precision cut short fibres, high surface area, miscible in blend composites, thermal resistance, excellent friction and wear resistance; cord, high tensile strength and modulus at low specific weight, retention of physical properties at high and low temperature extremes, very low heat shrinkage, very low creep, good fatigue resistance; fabric, excellent ballistic performance at low weights; and excellent resistance to cuts and protrusion combined with comfortable wear and excellent friction and wear performance against other materials.

The peptide fibrils and fibres of the disclosure may have a variety of applications, for example, in adhesives and sealants, e.g. thixotropes; in ballistics and defence, e.g., anti-mine boots, gloves—cut resistance police and military, composite helmets, and vests—bullet and fragmentation; in belts and hoses, e.g. automotive heating/cooling systems, automotive and industrial hoses, and automotive and industrial synchronous and power transmission belts; in composites, e.g., aircraft structural body parts and cabin panels, boats, and sporting goods; in fibre optic and electro-mechanical cables, e.g., communication and data transmission cables, ignition wires, and submarine, aerostat and robotic tethers; in friction products and gaskets, e.g., asbestos replacement, automotive and industrial gaskets for high pressure and high temperature environments, brake pads, and clutch linings; in protective apparel, e.g. boots, chain saw chaps, cut resistant industrial gloves, helmets—fireman and consumer (bicycle), and thermal and cut protective aprons, sleeves, etc; in tires, e.g. aircraft, automobiles, off-road, race, and trucks; and in ropes and cables, e.g., antennae guy wires, fish line, industrial and marine utility ropes, lifting slings, mooring and emergency tow lines, netting and webbing, and pull tapes.

Biomedical and Biomaterial Applications

Biocompatible surfaces: Bioresponsive and biocompatible surfaces to promote or to prevent adhesion, spreading and growth of endothelial cells in medical implant materials. Biocompatible surface coatings for devices such as stents, valves and other structures introduced into biological systems. Biocompatible surface coatings for dental implants and intra-oral appliances e.g. dental prosthesis.

Tissue Engineering:

The peptide fibrils and/or fibres of the disclosure can be used in the construction of a biodegradable three-dimensional scaffold for use in attaching cells to produce various tissues in vivo and in vitro.

Thus according to a further feature of the disclosure we provide a three-dimensional scaffold comprising fibres or fibrils of the disclosure in cell medium. As mentioned above such scaffolds of the peptide fibrils and/or fibres are advantageous in that they can be used to support cells in the growth and/or repair of tissue. The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte or osteoblast or other progenitor cells.

Therefore, according to a yet further feature of the disclosure we provide a three-dimensional scaffold comprising fibres or fibrils as hereinbefore described which scaffold is seeded with cells.

The methods of the disclosure therefore result in the efficient production of new ligament, tendon, cartilage, bone, skin, etc in vivo.

The cells may themselves be cultured in the matrix in vitro or in vivo. The cells may be introduced into the implant scaffold before, during or after implantation of the scaffold. The newly grown tissue can be used to hold the scaffold in place at the site of implantation and also may provide a source of cells for attachment to the scaffold in vivo.

The ability of the polymers to break allowing the free ends to self assemble enables, for example, scaffolds to be formed in situ and also to respond (by breaking and reforming) to the growing tissue. Also monomeric peptides may be injected at the site of choice and then chemically triggered to create, for example, a gel in situ.

Thus, according to a further feature of the disclosure we provide a method of tissue repair which comprises seeding a three-dimensional fibre matrix as hereinbefore described with appropriate cells.

For a tendon or ligament to be constructed, successfully implanted, and function, the matrices must have sufficient surface area and exposure to nutrients such that cellular growth and differentiation can occur following implantation. The organisation of the tissue may be regulated by the microstructure of the matrix. Specific pore sizes and structures may be utilised to control the pattern and extent of fibrovascular tissue in growth from the host, as well as the organisation of the implanted cells. The surface geometry and chemistry of the scaffold matrix may be regulated to control the adhesion, organisation, and function of implanted cells or host cells.

In an exemplary embodiment, the scaffold matrix is formed of peptides having a fibrous structure which has sufficient interstitial spacing to allow for free diffusion of nutrients and gases to cells attached to the matrix surface until vascularisation and engraftment of new tissue occurs.

The interstitial spacing is typically in the range of 50 nm to 300 microns. As used herein, "fibrous" includes one or more fibres that is entwined with itself, multiple fibres in a woven or non-woven mesh, and sponge-like devices.

Nerve Tissue Engineering:

The fibrils and/or fibres can be used to provide paths/tracks, to control and guide the direction of growth or movement of molecules or cells. This may be useful for nerve tissue repair as well as for growth and formation of bone tissue (tissue engineering).

Bone Tissue Engineering:

Biomineralisation using the peptide ribbons, fibrils and/or fibres as a template for the nucleation and growth of inorganic materials is important in bone tissue engineering and dental applications etc. The self assembled peptide structures have been shown to be effective as templates for hydroxyapatite crystallisation, as shown in the later examples.

Self-assembling complementary peptides may increase mineral gain via their ability to nucleate hydroxyapatite de novo and/or by decreasing mineral dissolution via stabilisation of mineral surfaces. They are therefore candidate materials for use in both caries treatment and prevention, in treatment for dentina sensitivity, in control of ectopic calcification and in treatment or prevention of bone defects and deterioration, such as that experienced in osteoporosis or in periodontitis.

The use of peptides, e.g., self assembling complementary peptides (SACPs), as scaffolds in in situ tissue engineering of bone is novel per se.

Thus according to a further aspect of the disclosure provided is a method of tissue engineering, e.g., tissue repair, such as of bone repair, which comprises the use of SACPs as a scaffold.

Artificial Skin:

Network structures formed from the peptide ribbons, fibrils or fibres can be used to generate artificial skin or to promote skin re-growth in vivo.

Drug Delivery:

pH and ion responsive ribbons, fibrils, fibres, gels or liquid crystals are potentially useful in drug encapsulation and release and by designing an appropriate network programmable release rates may be achieved.

Personal Care Products

Dental Applications:

Peptide ribbons, fibrils and/or fibres are of use in the protection of teeth, as carriers for delivery of active substances to promote dental repair, as templates/scaffolds for the in situ nucleation of hydroxyapatite within tooth porosities (e.g., caries lesions, dentine), as agents for the treatment and/or prevention of caries (enamel/dentine and marginal caries around restorations), as agents for the treatment and prevention of tooth sensitivity and as carriers for the delivery of active substances into teeth. In addition, the peptide structures are of application in the treatment of dentinal/tooth staining, sensitivity and other symptoms experienced in gingival recession. The use of self assembled complementary peptide structures in caries treatment is demonstrated in the later examples.

The prior art describes use of an amphiphilic peptide as a scaffold for ordered deposition of mineral imitating crystal orientation in bone collagen This amphiphilic peptide assembles to give a structure which forms fibrils which are stabilised by covalent modification. The assembly of this peptide differs from the self assembled peptides described here in that the assembly is driven by amphiphilic forces, rather than by very specific attractions between matched groups in the separate peptide chains. The amphiphilic peptide described is not suitable for treatment in vivo as the assembly must take place at low pH (pH<4) and the covalent modification takes place under conditions hostile to living tissues. The self assembled complementary peptide ribbons, fibrils and fibres described in this application differ in that they can be designed such that assembly is triggered merely by contacting each of the complementary peptides rather than by environmental conditions such as a pH with no subsequent reaction under hostile conditions is necessary.

The prior art also describes use of casein phosphopeptides in dental application These species are not self assembling peptides as described in this application. As shown in the examples, the self assembled peptides described in this application show improved performance in mineralisation of caries like lesions of enamel under simulated oral conditions compared with the casein phosphopeptides.

In particular, we provide a method as hereinbefore described wherein the method comprises the prevention, treatment and/or alleviation of dental caries. Thus the method may comprise the mineralisation or remineralisation of a dental cavity or the suppression of leakage around existing restorations. Alternatively, the method may comprise suppression of demineralisation.

In particular, we provide a method as hereinbefore described wherein the method comprises the prevention, treatment and/or alleviation of tooth sensitivity. Thus the method may comprise the remineralisation of a dental cavity, white spot lesions or exposed dentine. Alternatively, the method may comprise suppression of demineralisation, thus preventing development of tooth sensitivity.

Skin Treatments:

The controlled formation of peptide ribbons, fibrils and/or fibres can be of benefit in skincare and dermatological applications for both cosmetic and medical benefit. Benefits may include skin protection, improvement in skin feel, improvement of skin strength, increased suppleness, delivery of active or beneficial substances, moisturization, improved appearance and anti-ageing effects.

Hair care products: Peptide ribbons, fibrils and/or fibres can be of benefit in hair care to improve hair condition, strength, feel, suppleness, appearance and moisturisation. Peptides which form such structures in application can be beneficial ingredients in hair shampoos, conditioners, dyes, gels, mousses and other dressings.

In another aspect of the disclosure responsive networks can be used to deliver perfumes, vitamins and/or other beneficial agents to the skin and/or hair.

Example 1: Synthesis, Purification and Sterilisation of Peptides

Complementary peptides were synthesized using standard 9-fluorenylmethoxycarbonyl (FMOC) chemistry protocols as described in Aggeli et al. (*J. Mat. Chem.*, 7:1135, 1997). Peptides were purified by reversed-phase HPLC using a water-acetonitrile gradient in the presence of 0.1% trifluoroacetic acid or ammonia as buffer A and 10% buffer A in acetonitrile as buffer B. Mass spectrometry showed the expected molecular weights. Peptides were sterilized in the dry state using γ-irradiation (2.5 MRad) with a Gammacell 1000 Elite irradiator. TEM and mass spectrometry were used to assess any damage to the peptide structure and fibril formation.

Four pairs of systematically varied complementary peptides were designed following the design criterion of +2/−2 net charge per peptide pair that applies to single peptide gels in physiological solutions. In all cases, the individual peptides were found to be monomeric random coils and to form low viscosity solutions. Upon mixing, most of the complementary pairs led to instant gelation in physiological solution conditions, confirming that the +2/−2 net charge can be used as a design criterion not only for single peptides but also for complementary peptide gels.

Example 2: Comparative Gelation Studies

Samples of all complementary pairs $P_{11}$-13/14, $P_{11}$-26/27, $P_{11}$-28/29 and $P_{11}$-30/31 were prepared at concentrations of 2, 3, 5, 10, 15, 20 and 30 mg/ml. Peptides were weighed out (Mettler AE 240 balance) and diluted to produce the correct concentration, taking peptide purity into account, using DMEM solution (for dilution volumes and peptide weights of all sample produced see appendix 2). Small amounts of acid (HCl 1M, 0.5M or 0.1 M) and base (NaOH 1M, 0.1M) were added and gentle heating applied when the peptide did not fully dissolve. The monomer solutions were combined in a 1:1 molar ratio to produce a mixture of the 2 complementary peptides, once mixed the room samples were placed in an incubator (Labnet Mini Incubator, 9 liter, analogue, gravity convection) heated to 37° C. and left to reach equilibrium. Observations were carried out once a day over a one week period to determine the concentration at which gelation occurs therefore ascertaining when the system is at equilibrium. Table 2 below shows the comparative gelation studies in 2-30 mg mL-1 range of concentrations:

TABLE 2

| Peptide pair | Net charge | Hydrophobic character | Hydrogen bonding groups | C* gel in physiological solution and 37° C./ mg mL−1 | C*gel in physiological solution and 20° C./ mg mL−1 |
|---|---|---|---|---|---|
| P11-13/ 14 | −2 | Amphiphilic | —CONH2 | 7.5 ± 2.5 | 5.5 ± 1.5 |
| P11-28/ 29 | +2 | Amphiphilic | —CONH2 | 7.5 ± 2.5 (and 17.5 ± 2.5) | 4.0 ± 1.0 |
| P11-30/ 31 | −2 | Amphiphilic | —OH | 12.5 ± 2.5 | 27.5 ± 2.5 |
| P11-26/ 27 | −2 | Completely polar | —CONH2 | na | Na |

In all cases apart from $P_{11}$-26/27 gelation took place instantly upon mixing of the separate fluid peptide solutions at all concentration equal to or higher than c*gel. The formed gel remained stable over time during the observation time which was 1 week, confirming apparent equilibrium behaviour. Repeat experiments established full reproducibility of the reported behaviours. P11-13/14 gel also exhibited coloured birefringence when examined between cross polars, which is evidence of long range order in the material, ie the tapes partially align to form micro domains in the material with a common director for each microdomain. This may have important implications for the biological activity of the peptides, eg in the case of biomineralisation for the control of the direction of growth of hydroxypatite crystals. Birefringence was not reliably observed for the other pairs of peptides although further more detailed studies may show different results in the future. In the case of P11-28/29, two different c*gel values were observed in two different types of physiological like solutions, therefore these experiments will have to be repeated; however the overall gelation behaviour of this pair is likely to be very similar to P11-13/14 one. P11-13/14 and P11-28/29 have lower gelation concentrations compared to P11-30/31 and P11-26/27 did not form gels at all in physiological solutions, instead it tended to precipitate out of solution.

Example 3: Transmission Electron Microscopy Studies

Figure 5A:
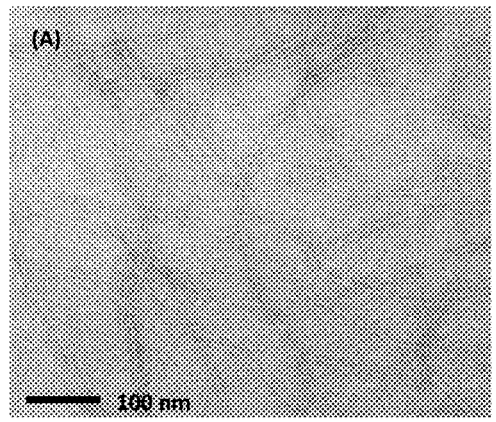
FIGS. 5A and 5B show TEM images of the complementary peptides $P_{11}$-13/14.
Figure 5B:
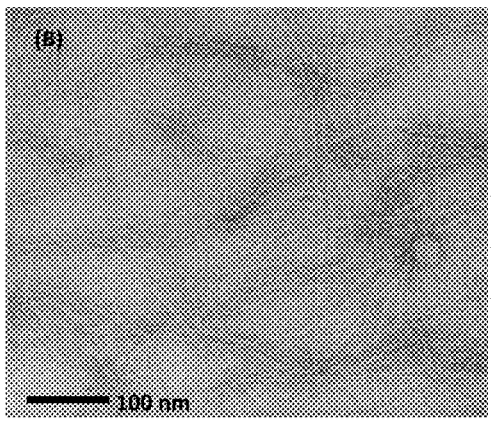

The room temperature $D_2O$ samples of all four complementary peptide pairs of concentration 15, 20, 30 mg/ml underwent TEM analysis. The samples in TEM are required to be very thin, around 40-60 nm thick, and are supported on a thin copper mess which offers a reasonable viewing area and are conductive enabling discharge of excess electrical charge produced by the electron beam to the microscope column. The copper grids are covered in a ultra thin carbon film which serves as an electron transparent support for the sample. Two small volumes of each sample were transferred to two different sample vials and diluted with $D_2O$ to produce two samples one with 15 and 50 times diluted. This dilution was carried out to ensure the sample, which when applied to the copper grids, would be thin and have a decreased salt content enabling the production of good TEM images. Carbon coated copper grids (Athene hexagonal 400 mesh copper 3.05 mm) were exposed to UV light for 30 minutes to charge the surface and ensure adhesion of sample to the surface. One drop of sample was applied to the carbon coated copper grids and left for one minute then the excess was removed using filter paper. The same process was repeated using 4% uranyl acetate solution but left for only 20 seconds. Uranyl acetate is used as a negative stain; it deflects the electron beam resulting in a dark section on the final image. A biological based sample, such as the peptides used in this research, does not absorb much of the uranyl acetate due to surface tension interactions which prevent it from penetrating the peptide aggregate and results in electrons being transmitted through the sample and reaching the detector. The grid surface is covered in the uranyl acetate which blocks the transmittance of electrons and produces the contrast between sample and background. Samples were then loaded into the TEM instrument (Philips CM10 operating at 80 kV) and pictures taken at various magnifications (39 k, 52 k and 73K). Once the image had been captured onto the film it was scanned onto a PC where it was then processed using Image J software to determine what type of aggregates were present and their widths. TEM studies revealed that P11-13/14 (FIG. 5) and P11-28/29 formed well defined, distinct aggregates of tapes with widths 4±1 and 6±1 respectively. P11-30/31 (FIG. 6) formed much looser associations of tapes (rather amorphous bundles), similar was also the behavior of P11-26/27 under the TEM.

Example 4: Scanning Electron Microscopy Studies

Samples of 15 mg/ml and 30 mg/ml in DMEM were produced for $P_{11}$-13/14 and $P_{11}$-30/31 using the same method previously outlined for the incubated DMEM samples. A small amount of gel was applied to the copper shim, with the excess liquid removed, and then frozen in liquid nitrogen. The samples were then freeze-dried (Peltier stage attached to a Polaron coating unit) and loaded with the stage running at approximately −65° C. and left for one hour. The stage is then warmed 10° C. every 30 minutes until room temperature is reached. Once dried the g majority of the gel is knocked off leaving a small amount in contact with the copper shim which is then mounted using carbon rods onto stubs. These were then splutter coated with approximately 3 nm of gold/palladium. The sample was then mounted into the SEM instrument and the images taken. The resulting images were processed using the Image J software to determine the width of the pores in the gel and also the width of the strands that produce the pores. SEM studies showed that P11-13/14 gel network consists of pore size of 900±750 at 15 mg mL-1 and 700±500 at 30 mg mL-1 (FIG. 7). Similar results were also obtained for P11-30/31 (FIG. 8).

Example 5: Spectroscopic (Mainly) FTIR Analysis

Figure 4:
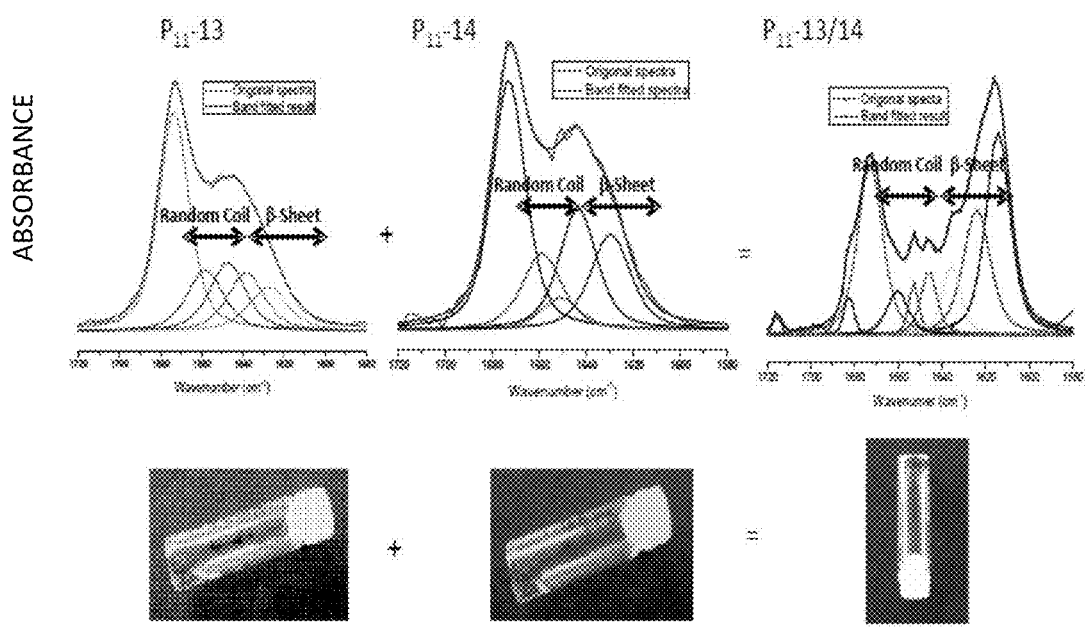
FIG. 4 shows the Fourier Transform Infrared Spectroscopy (FITR) analysis for the complementary peptides $P_{11}$-13/14 in isolation and in combination.

Samples for Fourier Transform Infrared Spectroscopy (FITR) analysis at both room and physiological temperature were prepared for $P_{11}$-13/14, $P_{11}$-26/27, $P_{11}$-28/29 and $P_{11}$-30/31 at concentrations of 2, 3, 5, 10, 15, 20 and 30 mg/ml. The peptide was dissolved in $D_2O$ (Aldrich Deuterium oxide, 99.9 atom % D) 130 mM NaCl (Fisher Scientific) solution to produce a known concentration of monomer solution in mg/ml. Gentle heating and, if required, small amounts of dilute DCl (Aldrich 35 wt. % in $D_2O$, 99 atom % D) and NaOD (Aldrich 40 wt. % in $D_2O$, 99 atom % D) were added to aid dissolution and correct the pD to near physiological conditions The monomer solutions of each peptide were combined, using a Gilson Pipetman P200, with a volume of its complementary peptide to produce a 1:1 molar ratio at a known overall concentration. $D_2O$ was used instead of $H_2O$ as its absorption in the amide I band is weak[13] and 130 mM NaCl is required to reproduce the ionic strength of physiological conditions allowing comparison with the DMEM samples. The purity of both $P_{11}$-13 and $P_{11}$-14 was 70.6% and 72.6% and so although not exactly 1:1 molar ratios were produced it is within a reasonable range. The concentrations produced were 3.8, 7.3, 10.8, 14.3 and 21.4 mg/ml. FIG. 4 shows the original and band filtered spectra for single and combined complementary peptides P11-13/14. The FTIR studies revealed that all the mixed complementary peptide solutions had very high content of beta-sheet (65-85%) even in the lowest concentration studied (5 mg mL-1). Further NMR studies at much lower concentrations revealed that c*tape for P11-13/14 and for P11-28/29 are very similar and in the region of 10-50 uM. This is much lower that c*tape for P11-4 which is at 400 uM. P11-30/31 c*tape is higher than 50 uM but still lower than 400 uM (further studies are required to define it accurately). Thus all complementary peptide pairs studied here have lower c*tape compared to P11-4, and therefore are likely to have much longer lifetime in vivo compared to "golden standard" P11-4 peptide.

Example 6: Mechanical Studies

Figure 9:
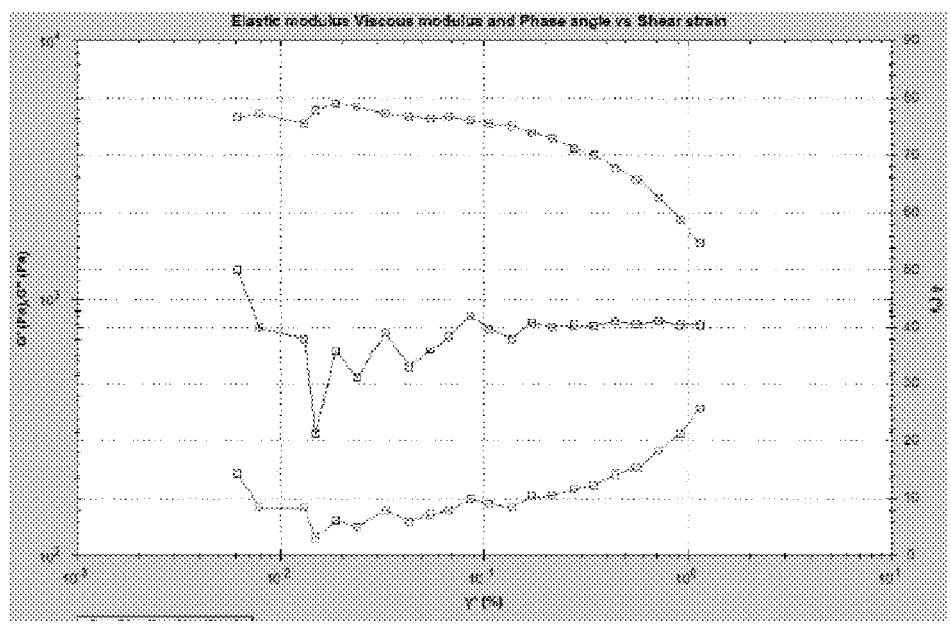
FIG. 9 shows the Elastic modulus, Viscous modulus and Phase Angle versus Shear strain for $P_{11}$-30/31 in physiological solution and temperature.

Mechanical studies established that the complementary peptide gels can have significant mechanical strength when considering that they are classified under soft matter. In particular P11-30/31 gels were characterised by a plateau elastic modulus of 4,000-5,000 Pa and a viscous modulus of 400-500 Pa. FIG. 9 shows the Elastic modulus, Viscous modulus and Phase Angle versus Shear strain for P11-30/31. Preliminary evidence suggests that depending on peptide design, the mechanical properties of the resulting complementary peptide gels may vary from as low as 20 Pa to as high as 80,000 Pa for the plateau elastic modulus. This wide range of mechanical properties give the opportunity to select gels of optimal mechanical strength to suit the requirements of different applications. For example in cases of applications of peptide gels as scaffolds for cell growth, different cell types require scaffolds with different mechanical strengths (stronger or softer) in order to thrive in them.

Example 7: Cytotoxicity Studies

Figures 10A, 10B:
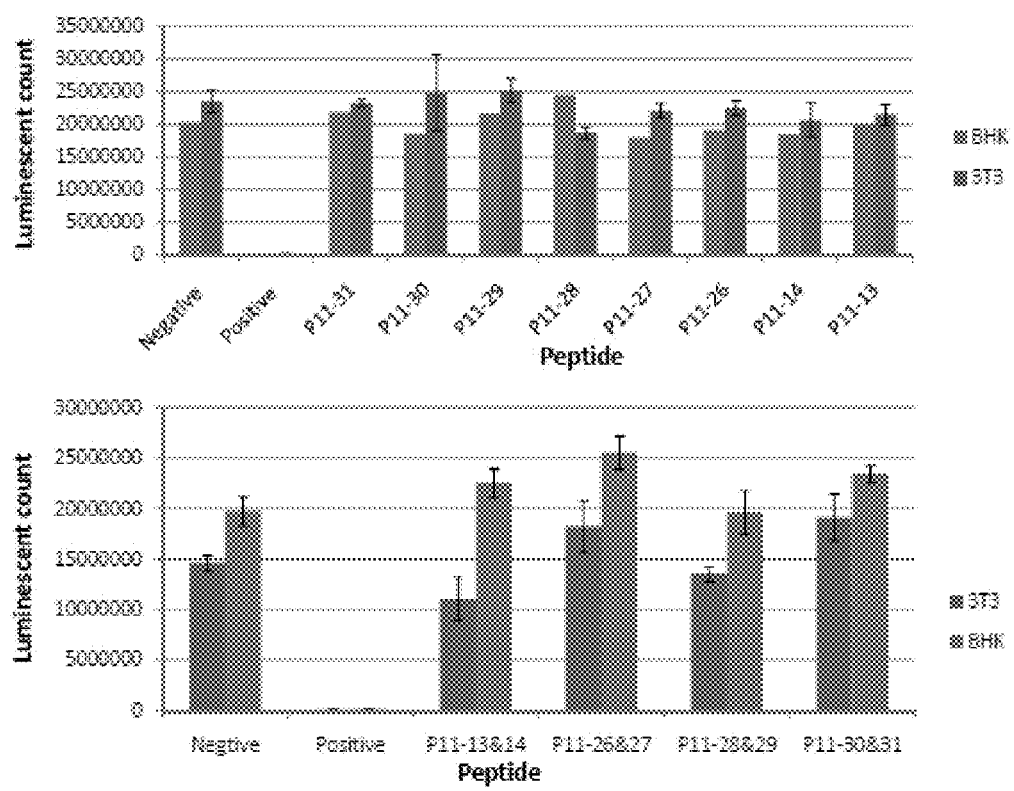
FIGS. 10A-10B show luminescent count toxicity studies in BHK and 3T3 cells for isolated complementary peptides (A) and combined complementary peptides (B).

Detailed cytotoxicity studies using the extract cytotoxicity method against two different cell types showed that all complementary peptides are biocompatible in their monomeric, low viscosity solution state and they don't show any statistical difference from the control sample. Self-assembling tapes of complementary peptide pairs were also tested for biocompatibility using the same method. All pairs were again found biocompatible with no statistically significant difference between any of these pairs and the control samples (FIG. 10).

The invention claimed is:

1. A pair of self assembling complementary polypeptides (SACPs) that form tapes, ribbons, fibrils or fibres in a β-sheet tape-like substructure, when a first monomeric peptide is contacted or mixed with its complementary monomeric peptide and wherein the SACPs comprise $P_{11}$-30/31 (SEQ ID NOs: 8 and 9).

2. The SACPs of claim 1, further comprising a bioactive peptide or a therapeutically active molecule conjugated to the SACPs.

3. A composition, comprising:
   tapes, ribbons, fibrils or fibres, wherein each of the tapes, ribbons, fibrils or fibres has an antiparallel arrangement of SACPs in a β-sheet tape-like substructure, wherein the SACPs comprise $P_{11}$-30/31 (SEQ ID NOs: 8 and 9).

4. The composition of claim 3, wherein the composition comprises SACPs which form ribbons and/or fibrils immediately when a first monomeric peptide contacts a second complementary monomeric peptide.

5. The composition of claim 3, wherein the SACPs further comprise a bioactive peptide or a therapeutically active molecule conjugated to the SACPs.

6. The composition of claim 3, wherein the composition comprises fibrils, and wherein the fibrils are comprised in a network of fibrils interconnected at fibre-like junctions.

7. A dental product comprising the composition of claim 3.

8. The dental product of claim 7, wherein the dental product is a dental repair, dental treatment, or dental reconstruction product.

9. The composition of claim 3, wherein the composition is in the form of a tissue engineering scaffold.

10. The composition of claim 9, wherein the scaffold is seeded with cells.

11. The composition of claim 3, wherein the composition is part of a bioresponsive and biocompatible surface.

12. The composition of claim 3, wherein the composition is a template for nucleation and growth of inorganic materials.

13. The composition of claim 3, wherein the composition comprises a continuous filament yarn, staple, floc, cord, or fabric.

14. A tissue repair product comprising the composition of claim 3.

15. A wound healing product comprising the composition of claim 3.

16. A skin treatment product comprising the composition of claim 3.

17. A hair care product comprising the composition of claim 3.

18. A bone reconstruction product comprising the composition of claim 3.

* * * * *